(12) United States Patent
Kedzie et al.

(10) Patent No.: US 7,655,396 B1
(45) Date of Patent: Feb. 2, 2010

(54) METHODS FOR DETECTING RECEPTOR MODULATOR ACTIVITY

(75) Inventors: Karen M. Kedzie, Rancho Santa Margarita, CA (US); Sandhya Rao, Irvine, CA (US); Daniel W. Gil, Corona Del Mar, CA (US); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/855,858

(22) Filed: Sep. 14, 2007

Related U.S. Application Data

(60) Provisional application No. 60/827,617, filed on Sep. 29, 2006.

(51) Int. Cl.
*C12Q 1/00* (2006.01)
*C07K 14/705* (2006.01)

(52) U.S. Cl. .......................................... 435/4; 530/350

(58) Field of Classification Search ........................ None
See application file for complete search history.

(56) References Cited

U.S. PATENT DOCUMENTS 5,707,798 A  1/1998 Brann

OTHER PUBLICATIONS

Coward et al., *Chimeric G proteins allow a high-throughput signaling assay of Gi-coupled receptors*. Anal Biochem.270(2):242-248, 1999.*

FLIPR Calcium Assay Kit, Molecular Devices Corporation, pp. 1-6, Nov. 2000.*

Hildebrandt, J. D., *Role of subunit diversity in signaling by heterotrimeric G-proteins*, Biochem Pharmacol., 54:325-339, (1997).

Jensen et al., *Pharmacological characteriazation of human excitatory amino acid transporters EAAT1, EAAT2 and EAAT3 in a fluorescence-based membrane potential assay*, Biochem. Pharmacol., 67:2115-2127, (2004).

Delegeane et al., *Tissue-Specific Enhancer of the Human Glycoprotein Hormone α-Subunit Gene: Dependence on Cyclic AMP-Inducible Elements*, Mol. Cell. Biol., 7: 3994-4002, (1987).

Seed et al, *A simple phase-extraction assay for chloramphenicol acyltransferase activity*, Gene, 67: 271-277, (1988).

Lomasney, J.W. et al., *Expansion Of The Alpha 2-Adrenergic Receptor Family: Cloning And Characterization Of A Human Alpha 2-Adrenergic Receptor Subtype, the Gene for which is located on Chromosome 2*, Proc. Natl. Acad. Sci. U.S.A. 87 (13), 5094-5098, (1990).

Regan, J.W. et al., *Cloning and expression of a human kidney cDNA for an alpha 2-adrenergic receptor subtype*, Proc. Natl. Acad. Sci. U.S.A. 85(17), 6301-6305, (1988).

Aiyar et al., *Human AT1 receptor is a single copy gene: characterization in a stable cell line*. Mol. Cell. Biochem. 131: 75-86, (1994).

* cited by examiner

*Primary Examiner*—Ruixiang Li
(74) *Attorney, Agent, or Firm*—Joel B. German; Debra Condino; Dean G. Stathakis

(57) ABSTRACT

Disclosed herein are methods of screening compounds that modulate G-protein coupled receptors. The assays are performed at temperatures of between about 25° C. and 40° C.

4 Claims, 11 Drawing Sheets

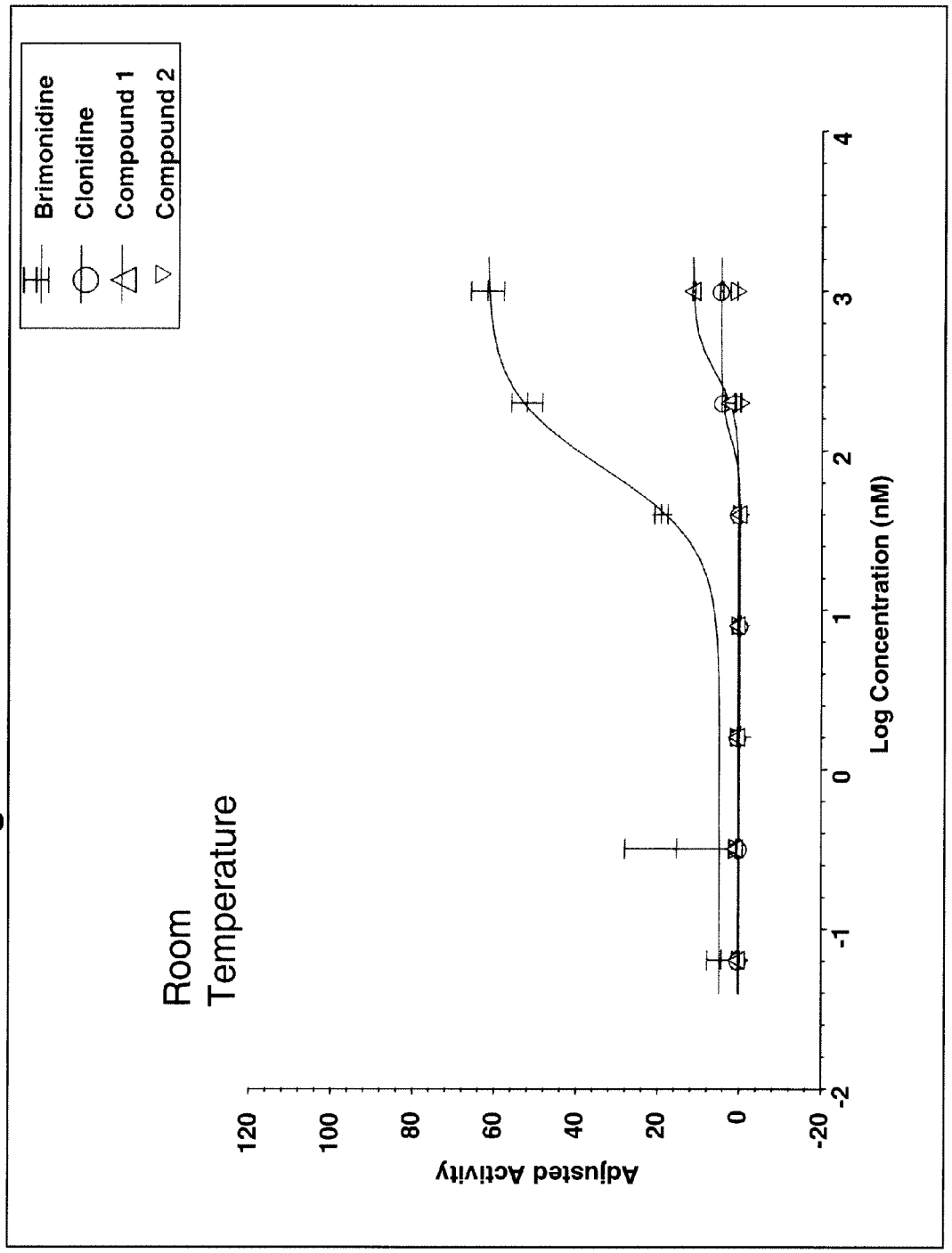

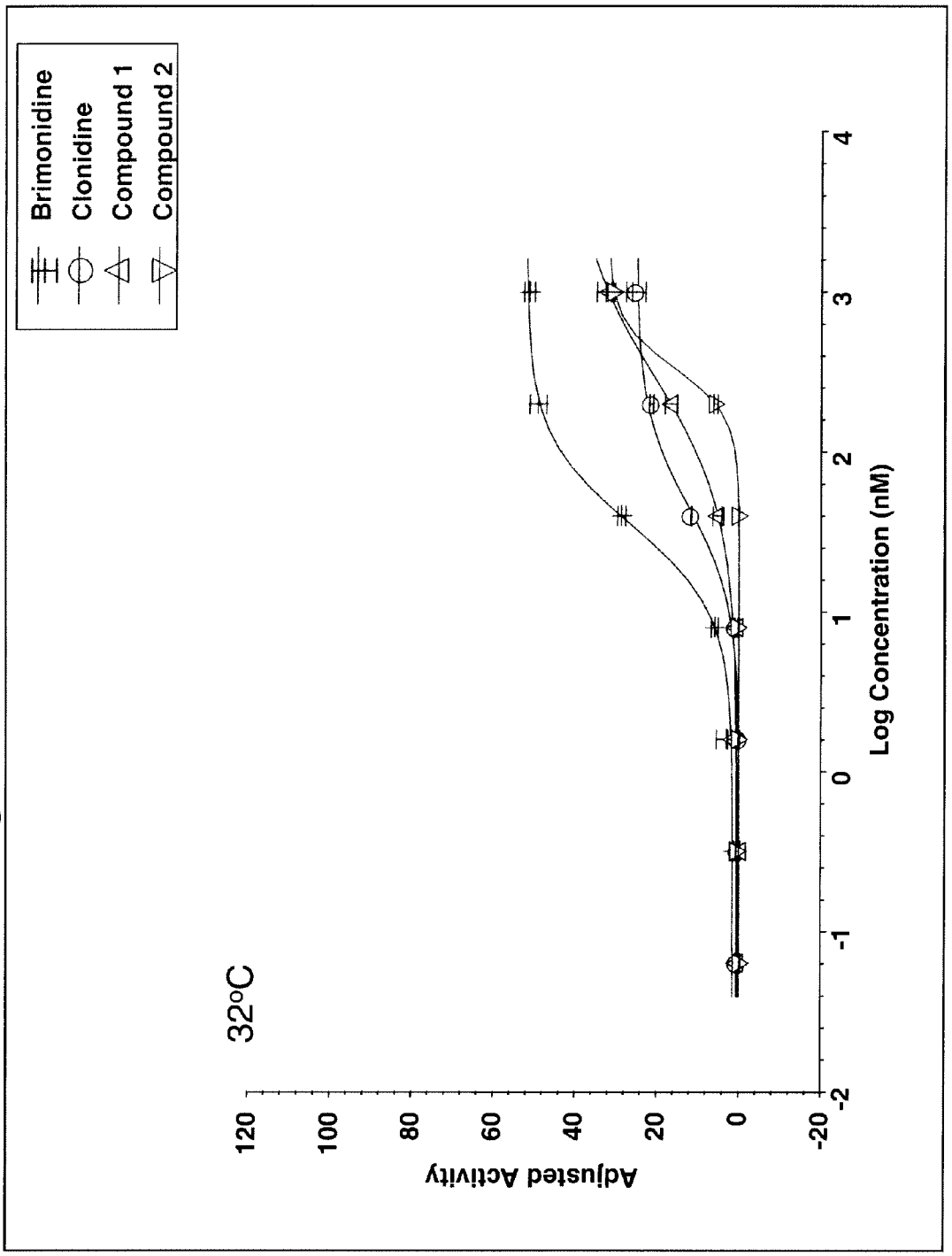

METHODS FOR DETECTING RECEPTOR MODULATOR ACTIVITY

CROSS REFERENCE TO RELATED APPLICATIONS

This application is based on, and claims the benefit of, U.S. Provisional Application No. 60/827,617, filed Sep. 29, 2006, and which is incorporated herein by reference.

The cells of higher organisms respond to biochemical signals from other cells in order to carry out the work necessary for the development, growth, and continued survival of the organism. Most of these signals are transmitted from outside the cell by means of cell surface receptors; these cell surface receptors are able to selectively respond to one or more specific or selective biochemical signal that binds to the extracellular domain of the receptor.

Cell surface receptors tend to fall within one of three categories: the channel-linked receptors (transmitter-gated ion channels involved in rapid synaptic signaling, as in nervous tissue or the neuromuscular junction); catalytic receptors (such as the insulin receptor, usually containing a protein (e.g., tyrosine) kinase domain); and the G-protein coupled receptors.

Regardless of the type of cell surface receptor, the intracellular response to ligand binding involves changes such as phosphorylation and dephosphorylation reactions, ion flux, changes in protein and/or nucleic acid synthesis, and changes in the intracellular transport of molecules. In neural and muscle cells, the cellular responses to ligand binding, whether the receptor is enzymatic, ion channel, or G-protein coupled, are particularly likely to involve the influx or efflux of ions and the cytoplasmic sequestering or liberation of ions.

When G-protein coupled receptors are bound to a specific ligand, the receptors indirectly activate or inactivate a separate plasma membrane-bound enzyme or ion channel. The interaction between the receptor and the affected enzyme or ion channel is mediated by a GTP binding protein, or "G-protein". G-protein coupled receptors initiate a cascade of chemical events within the target cell that usually alter the concentration of small intracellular messengers such as cyclic adenosine monophosphate (cAMP) or inositol triphosphate (ITP), as well as ions such as $Ca^{++}$.

The G-proteins themselves comprise any of a family of structurally similar heterotrimeric GTP-binding proteins that are associated with the intracellular portion of the plasma membrane, that bind activated receptor complexes and, through conformational changes and hydrolysis of GTP, directly or indirectly effect alterations in channel gating and cellular enzyme activity and so couple cell surface receptors to intracellular responses. The three subunits of a G-protein heterotrimer are $G\alpha$, $G\beta$ and $G\gamma$. The $\alpha$-subunits are unique to each G-protein, conferring functional specificity. The $\alpha$-subunits are subdivided into four major families on the basis of their amino acid sequence homology: 1) $Gs\alpha$ and Golf; 2) $G\alpha i$-1, $G\alpha i$-2, $G\alpha i$-3, $Go\alpha$, $Gz\alpha$, transducins 1 and 2, and gustducin; 3) $Gq\alpha$, $G11\alpha$, $G14\alpha$, and $G15\alpha$; and 4) $G12\alpha$ and G13; this list is very likely incomplete—indeed, splice variants of $Gs\alpha$, $G\alpha i$-2, and $Go\alpha$ as well as additional subfamily members of $\alpha$-subunits have recently been identified. In addition, five $\beta$-subunits and at least 10 $\gamma$-subunits have so far been described. See e.g., Hildebrandt, J. D., *Role of subunit diversity in signaling by heterotrimeric G-proteins*, BIOCHEM. PHARMACOL. 54:325-339 (1997).

G-proteins form trimers. Heterotrimeric G-proteins couple to G-protein coupled receptors. GPCRs are members of the class of receptors known as "serpentine" receptors; helical domains of the G-protein coupled receptors cross the plasma membrane seven times with an extracellular amino terminus and intracellular carboxyl terminus. G-protein coupled receptors are estimated to occur in more than 1000 variations in mammals and regulate some activity in nearly every human cell. The coupling of G-protein coupled receptors to heterotrimeric G-proteins is selective and specific in nature.

Not all ligands are associated with only one receptor or receptor type; thus a given ligand may selectively bind, for example, both an intracellular receptor and a cell surface receptor. Moreover, many receptors have different forms (which may be genetically distinct) and many of these various types can be further diversified by being expressed as isoforms, which may vary as to their tissue distribution and/or the disease state of the animal. Many or most of these forms or isoforms may normally bind a single ligand in vivo.

Ligands are compounds that constitute biochemical signals binding to the relevant receptor with a degree of selectivity or specificity. If the biochemical signal is an activator or "agonist" of the receptor, receptor binding will cause a change in the activity and/or conformation of the receptor, with the end result being a change in the activity of the cells. Conversely, the binding of a receptor "antagonist" may, for example, competitively or non-competitively inhibit the activation of the receptor by an agonist, thus making the cell at least temporarily unresponsive to extracellular stimuli. In this case, the lack of response may result in no change in the activity of the cells.

In addition to receptor agonists and antagonists, an "inverse agonist" is a compound that, while binding the receptor, actually causes a change in receptor activity that is contrary to the effect of a receptor agonist. Thus, for example, a receptor inverse agonist may decrease an activity to a level below that seen in the absence of a ligand; an antagonist of the same receptor may prevent such activation.

Also, certain compounds are termed "partial agonists" of a given receptor. These compounds are able to bind the receptor and have a stimulatory effect, but the maximum level of stimulation (efficacy) is less than that of a "full" agonist. Partial agonists thus share characteristics of a receptor agonist and a receptor antagonist, since the compound, while moderately activating the receptor, blocks full activation of the receptor by a full agonist. As an example, the bronchodilator isoproterenol is a full agonist, and the drug prenalterol is a partial agonist, for $\beta$-adrenergic receptors (a class of G-protein coupled receptors) in some tissues. A drug that acts as a partial agonist in one tissue or at one receptor class may act as a full agonist in another.

The differences between the maximal effects of two or more drugs relates to the relative "efficacy" of these drugs; efficacy is to be distinguished from "potency" which is described using a calculation of the drug concentration at which 50% of that drug's maximal efficacy is seen (known as the "$EC_{50}$"). Two drugs may have similar or different potencies at the same receptor and independently have similar or different efficacies, and vice versa. Indeed, virtually any two agonists at the same receptor have maximal effects that differ from each other, and the drug having the lower efficacy can be considered a partial agonist when compared to the other compound. Nevertheless, a partial agonist is defined herein as a compound having maximal agonist activity less than that of the naturally occurring agonist.

The present invention provides methods useful with methods of screening, particularly including high throughout assays, which can rapidly demonstrate whether a given compound is (or is not) an agonist of a G-protein-coupled receptor.

The present invention provides methods for the identification of agonists and antagonists, full or partial, comprising contacting a test compound with a receptor at a constant temperature greater than room temperature and less than 40° C. under conditions permitting the activity of such receptor to be detected, and detecting the ability of such compound to stimulate the activity of said receptor.

The present invention comprises assay methods in which the temperature is greater than 23° C. and below 40° C. Preferably, the temperature is between about 32° C. and about 37° C.; even more preferably between about 35° C. and about 37° C.; still more preferably, about 37° C. or precisely 37° C.

One can detect partial agonists and antagonists by the following method:
 a) contacting, at a temperature of about 25° C. or less, a test compound with a cell expressing the receptor;
 b) detecting a change in the level of activity of the receptor;
 c) contacting, at a temperature of about 35° C. or higher, a test compound with a cell expressing the receptor;
 d) detecting a change in the level of activity of the receptor; and
 e) comparing the result obtained in step a) with the result obtained in step d); a compound that shows no activity at temperatures closer to room temperature but does show activity at temperatures closer to physiological temperature is likely to be a partial agonist or antagonist.

In receptor systems that involve a change in membrane potential (such as receptors involving ion channels) until recently, the method of choice for measuring changes in membrane potential has been patch clamping. Although slow and labor-intensive (termed as an "ultra low throughput" assay method), this technique is the most highly informative and is considered the "gold standard" for the analysis of ion channels.

Automated patch-clamping assay systems have recently been made available, and are sold by companies including, without limitation, Sophion Biosciences of Copenhagen, Denmark (the Apatchi™ and Qpatch™ systems) and Cytocentrics CCS GmbH of Reutlingen, Germany (the Cytopatch™ system.)

With regard to GPCRs which are involved in the stimulation or inhibition of cellular growth through the regulation of cellular enzyme activity, one method for detecting agonists or antagonists of GPCRs involves the expression of receptors contained in cell types whose growth is affected by a receptor agonist or antagonist. An exemplary assay is described in U.S. Pat. No. 5,707,798, the disclosure of which is incorporated by reference in its entirety; changes in growth can be observed through observation of the enhanced expression of a marker gene. Such a marker gene may comprise, without limitation, an enzyme, a binding protein, or an antigen. Cells that respond to stimulation or inhibition of signal transduction through a change in cellular growth include: NIH 3T3 mouse fibroblast cells (ATCC CRL 1658), which respond by growth to stimulation of Gq-coupled and tyrosine kinase receptors; RAT 1 cells, which respond to changes in cAMP mediated by Gi- and Gs-coupled receptors; and pituitary cells, which also respond to changes in cAMP mediated by Gi- and Gs-coupled receptors.

Methods of transfecting mammalian cells are commonly known, and disclosed in various papers and books, including Sambrook & Russell, MOLECULAR CLONING: A LABORATORY MANUAL (3d ed. Cold Spring Harbor Laboratory Press 2001), hereby incorporated by reference in its entirety. Such transfection may be transient, in which the recombinant receptor gene is not incorporated into the host cell genome, or stable in which case genomic integration is promoted. Depending in part on the cell types sought to be transfected, these methods may involve techniques including lipid-mediated transfection, calcium phosphate mediated transfection, DEAE-dextran mediated transfection, electroporation, biolistics, and Polybrene-mediated transfection. All of these (except the DEAE-dextran method which is useful only for transient transfection) can be used for stable or transient transfection, with stable transfection occurring at a frequency roughly 2 orders of magnitude less than transient transfection.

Examples of markers which may be used to monitor an increase or decrease in cell numbers include enzymes useful as markers are phosphatases (such as acid or alkaline phosphatase), β-galactosidase, urease, glucose oxidase, carbonic anhydrase, acetylcholinesterase, glucoamylase, malate dehydrogenase, glucose-6-phosphate dehydrogenase, β-glucosidase, proteases, pyruvate decarboxylase, esterases, luciferase, alcohol dehydrogenase, or peroxidases (such as horseradish peroxidase).

To detect enzyme activity, a substrate must be added to catalyse a reaction the end product of which is detectable. Examples of substrates which may be employed in the method according to the invention include o-nitrophenyl-β-D-galactopyranoside, 5-bromo-4-chloro-3-indolyl-β-D-galactopyranoside, chloronaphthole, o-phenylenediamine, 3-(p-hydroxyphenyl) propionic acid, luminol, indoxyl phosphate, p-nitrophenylphosphate, nitrophenyl galactose, 4-methyl umbelliferyl-D-galactopyranoside, $H_2O_2$/tetramethylbenzidine or luciferin. In this type of assay system assay system, the marker is preferably β-galactosidase or firefly luciferase.

Another method for detecting agonists or antagonists of those receptors whose activation is associated with ion flux (or can be made to be) is the use of voltage-sensitive and ion indicator dyes, particularly when used in conjunction with a high-throughput detection method, such as the FLIPR® (Fluorometric Imaging Plate Reader) system, manufactured and sold by Molecular Devices Corp. Such an assay system requires pre-loading cultured cells displaying the desired receptor with a dye, then exposing the cell to a prospective receptor ligand and detecting an increase or decrease in intracellular fluorescence as a result of ligand-dependent receptor activation or inactivation, or inhibition of such ligand-dependent activity. Detection can involve, for example, the appearance or disappearance of fluorescence, or can involve the use of e.g., confocal photomicroscopy perhaps coupled with the use of computer software to monitor changes in the amount of intracellular distribution of a dye or other label, such as between membrane and cytoplasm or nucleus and cytoplasm.

Many available dyes have several limitations, including slow response times that do not provide the same level of information as patch clamping in assays of membrane potential. Assays employing such dyes may utilize temperature stabilization techniques in an attempt to increase response times, or to enhance reproducibility between assays; however until now it has always been generally considered as desirable to utilize dyes that do not require temperatures other than room temperature.

The FLIPR® membrane potential assay system utilizes a reagent system that is said to provide very high throughput while showing good correlation with information that can be obtained with manual patch clamping.

Certain FLIPR® reagent systems allow for elimination of wash steps and much shorter read times on the instrument. Using the dye contained in the Molecular Devices Membrane Potential Assay System, for example, it is said that data for a 384-well plate can be collected in less than 2 minutes, as opposed to up to 30 minutes with other dyes, such as the proprietary dye DiBAC, marketed by Molecular Probes, Inc. And because the dye in the Membrane Potential Assay Kit is much less sensitive to temperature changes than DiBAC, plates can be set up ahead of time and stacked for batch runs, making the assay highly amenable to automation. Such stacking usually occurs at room temperature.

Other methods of measuring receptor activity include monitoring the intracellular levels of cAMP, IP3, and/or other "second messengers" in response to exposure to a potential ligand.

In an embodiment the invention is also drawn to methods for the high-throughput assay of potential GPCR modulators, comprising conducting such assays at a temperature between room temperature (about 23° C.) and about 40° C. Preferably, the temperature is greater than about 30° C. and below about 40° C. Preferably, the temperature is between about 32° C. and about 37° C.; even more preferably between about 35° C. and about 37° C.; still more preferably, about 37° C. or precisely 37° C. The Applicants have discovered that performing such assays at temperatures closer to physiological temperature (37° C.) will result in the identification of some compounds (such as partial agonists) that will not be found at room temperatures. Therefore using such temperatures consistently for the identification of modulators of GPCRs, particularly in high volume formats (such as high throughput screening ("HTS")) will lead to an optimization of such assay procedures under conditions closer to those encountered in vivo, and the identification of compounds of interest more rapidly.

Some detailed examples of "low throughput" assay formats are provided in, for example, Jensen et al., *Biochem. Pharmacol.* 67:2115-2127 (2004), which describes the pharmacological characterization of the amino acid transporters EAAT 1, EAAT 2 and EAAT3. These receptors are members of the family of sodium-dependent high affinity glutamate/aspartate transporters, and are responsible for the reuptake of L-glutamate ("L-Glu"; the major excitatory neurotransmitter) from the synaptic cleft. The receptors use the cellular Na+/K+ gradient as a driving force for the transport of an L-Glu molecule plus 3 sodium ions and one proton, and the counter-transport of one $K^+$ ion. Additionally, an uncoupled $Cl^-$ flux is also associated with the transport. As L-Glu can act as a neurotoxin at high concentrations, these transporters may be important targets for finding drugs effective as neuroprotectants or therapeutics for the treatment of Alzheimer's Disease, amylotropic lateral sclerosis (ALS), cerebral ischemia, and stroke.

Jensen describes two different activity assay systems for measuring the pharmacological activity of putative receptor ligands in Human Embryonic Kidney cells (HEK 293 cells) transfected with recombinant EAAT1, EAAT2 or EAAT3: a) a conventional [$^3$H]-D-aspartate or [$^3$H]-L-Glu uptake assay, and b) a fluorescence-based FLIPR® Membrane Potential Assay.

The [$^3$H]-D-aspartate/[$^3$H]-L-Glu uptake assay is carried out as follows: cell lines transfected with the cell surface receptor-encoding nucleic acids (in this case, EAAT1-, EAAT2-, and EAAT3-containing HEK293 cells) are plated into poly-D-lysine coated white 96-well plates in DMEM (Delbecco's Modified Eagle's Medium) supplemented with each of 100 U/ml penicillin and 100 U/ml streptomycin, 10% bovine serum albumin (BSA) and 1 mg/ml G-418 antibiotic. After 1 day the medium was aspirated and cells were washed three times with 100 microliters of assay buffer (Hank's Buffered Saline Solution plus 1 mM $CaCl_2$ and 1 mM $MgCl_2$).

Fifty microliters of assay buffer supplemented with the radioligand and various concentrations of different ligands is added to each well, and the plate incubated at 37° C. for 15 minutes. Each well is then washed three times with 100 microliters of ice-cold assay buffer and 150 microliters of scintillation fluid added to each well. The plate is now shaken for one hour and the radioactivity counted in a scintillation counter. Each experiment is performed in duplicate three or four times for each compound. Concentrations of [$^3$H]-D-aspartate or [$^3$H]-L-Glu are up to 300 nM.

The FLIPR® assay is described as follows: the dye in this case is a lipophilic, anionic, bis-oxonol dye obtained from Molecular Devices Corp.; the dye is excited at 530 nm. The distribution of this dye across the cell membrane is dependent on the membrane potential of the cell such that depolarization of the cells permits more dye to enter the cells causing an increase in fluorescence. The opposite effect is seen on hyperpolarization of the cell.

Cells are split into poly-D-lysine-coated black clear bottom 96 well microtiter plates in DMEM supplemented with each of 100 U/ml penicillin and 10 U/ml streptomycin, 10% bovine serum albumin (BSA) and 1 mg/ml G-418 antibiotic. After 24 hours the cells were washed once with 100 microliters of Krebs buffer (140 mM NaCl, 4.7 mM KCl, 2.5 mM $CaCl_2$, 1.2 mM $MgCl_2$, 11 mM HEPES, 10 mM D-glucose, pH 7.4), and then provided 100 microliters of Krebs buffer containing the bis-oxonol assay dye. The plate was then incubated at 37° C. for thirty minutes and assayed at room temperature in a NOVOstar™ plate reader (BMG Labtechnologies, Offenburg, Germany). Fluorescent emission from each sample was measured at 560 nm from excitation at 530 nm; measurement was continued before and up to 1 minute after the addition of 25 microliters of a solution containing the prospective ligand.

Another commonly used assay format is the detection of cAMP formation after incubation of the receptor and prospective ligand together. Since cAMP is a second messenger in upon stimulation of receptors such as G-protein coupled receptors (GPCRs), detection of the formation of cAMP, such as by antibodies, is a measure of receptor activation.

In an exemplary assay, cell membranes are harvested from a cell line known to contain the GPCR in question, using hypotonic 25 mM HEPES buffer (pH 7.4), 1 mM EDTA, 20 micrograms/ml leupeptin, 1 mM PMSF (phenylmethylsulfonyl fluoride, as a protease inhibitor) with scraping followed by differential centrifugation to isolate the membrane fraction.

Membranes are incubated in 25 mM Tris (pH 7.6), 0.2% BSA, 2.6 mM Mg, 0.8 mM ATP, 0.1 mM GTP, 5 mM creatine phosphate, 50 U/ml creatine kinase, 0.2 mM IBMX at 32° C. Prospective ligands are added and incubation is continued for another 15 minutes. The amount of cAMP produced is assayed using an fluorescent immunoassay method.

Intact cell cAMP assays can be performed using suspended receptor-containing cells removed from culture flasks by trypsin treatment. Cells are preincubated with 0.5 mM 3-isobutyl-1-methylxanthine (IBMX, an inhibitor of cAMP-dependent phosphatase activity) at 37° C. Prospective ligands are added and incubation continued for 15 minutes; incubation is stopped by heating the suspension in boiling water. The amount of cAMP or cGMP resulting from these incubations can then be assayed by RIA using the appropriate anti-cyclic nucleoside monophosphate antibody.

Alternatively, other cAMP assay methods may involve the cotransfection of nucleic acids encoding the receptor, such as the G-protein coupled receptor, with a cAMP-dependent chloramphenicol acetyl transferase (CAT) reporter plasmid into human JEG-3 choriocarcinoma cells, and challenging the cells with modulators of the receptor. Due to the laborintensiveness of this assay, it, like certain other assay formats disclosed herein, are not adaptable to high volume, high throughput screening.

For example, human JEG-3 cells (American Type Culture Collection, Rockville, Md.) are cultured in Delbecco's Modified Eagle's Medium (DMEM) containing 10% fetal calf serum (FCS), 100 units/ml penicillin, and 100 micrograms/ml streptomycin. Cells are plated in 10 cm dishes 1-2 days before transfection. Cells are then transfected with 10 micrograms of a CAT reporter such as plasmid TESBgIIICRE(+)Δ NHSE (provided by P. Mellon, Salk Institute, La Jolla, Calif.) containing an 18 base pair cyclic AMP responsive element from the promoter of the α-subunit gene for the human glycoprotein hormones linked to the herpes simplex virus thymidine kinase promoter in turn linked to CAT (Delegeane et al., (1987) Mol. Cell. Biol., 7: 3994-4002), and 10 micrograms of the relevant receptor plasmid, using the calcium phosphate precipitation technique (Graham and van der Eb, (1973) Virology, 52: 456-467). After transfection, cells are maintained in DMEM/5% FCS for 36-40 hours, and then rinsed twice with DMEM. Forskolin (1 µM), a drug known to stimulate adenylate cyclase activity, can then be added in 5 ml DMEM as a positive control, along with the test compounds. Cells are then incubated for 4 hours at 37° C. and harvested.

For the CAT assay, after drug incubations cells are rinsed with cold PBS and scraped into 1 ml 40 mM Tris-HCl, pH 7.5, 150 mM NaCl, 1 mM EDTA. Cells are centrifuged and lysed by 3 cycles of freeze-thaw in 200 µl 250 mM Tris-HCl, pH 7.5 ($^3$H)-CAT assays are performed using 50 µl cytosol, 200 nCi [$^3$H]-chloramphenicol and 300 µM butyryl-CoA (Seed and Sheen, (1988) Gene, 67: 271-277). Samples are incubated for 1 hour at 37° C. and reactions stopped with the addition of 200 µl mixed xylenes. Butyrylated chloramphenicol is extracted into mixed xylenes which were then back-extracted twice with 200 µl 10 mM Tris-HCl, pH 8.0, 1 mM EDTA. Radiolabeled product is measured by liquid scintillation counting using a Packard Tri-Carb 460C at 50-52% efficiency. Increased CAT activity, indicated by transfer of butyryl groups from butyryl CoA to [$^3$H]-chloramphenicol, is a measure of increased cAMP accumulation.

Another assay of GTPase activity (this one routinely carried out at room temperature for "convenience") can be carried out as follows: confluent cells are harvested from tissue culture plates using PBS. The cells are then centrifuged at 300×g for 5 minutes at 4° C. The pellet is suspended in cold lysis buffer (5 mM Tris/HCl, 5 mM EDTA, 5 mM EGTA, 0.1 mM PMSF pH 7.5) using a Polytron Disrupter sonicator and centrifuged at 34,000×g for 15 minutes at 4° C. The supernatant is discarded and the pellet again resuspended in lysis buffer and centrifuged as above. Finally the membrane preparation is suspended in membrane buffer (50 mM Tris/HCl, 1 mM EDTA, 5 mM MgCl$_2$, 0.1 mM PMSF pH 7.4.)

The radioligand [$^{35}$S]-GTPγS (having a specific activity of 1250 Ci/mmole) is used for the assay. The frozen membrane aliquots were thawed and diluted in incubation buffer (50 mM Tris/HCl, 1 mM EDTA, 5 mM MgCl$_2$, 100 mM NaCl, 1 mM DTT, 1 mM propanolol, 2 µM GDP, pH 7.4) and incubated with the radioligand (at a final concentration of 0.3 nM) for 60 minutes at 25° C. At the end of the incubation period the samples are filtered through glass fiber filters (Whatman GF/B pretreated with BSA) in a 96 well cell harvester and rapidly washed 4 times with 4 ml ice-cold wash buffer (50 mM Tris/HCl, 5 mM MgCl$_2$, 100 mM NaCl, pH 7.4). The filters are then oven dried and transferred to scintillation vials containing 5 ml scintillation fluid.

A common FRET-based cAMP assay (AlphaScreen cAMP Functional Assay, PerkinElmer Life and Analytical Sciences Inc.) also is conducted at "room temperature" according to the manufacturer's directions, although the manufacturer suggests "for consistent results the same incubation time and temperature should be used for each plate". See Perkin Elmer Catalog Numbers 6760625D, 6760625M, and 6760625R and accompanying documentation available from the Perkin-Elmer website and entitled cAMPKits.pdf, hereby incorporated by reference herein. The FRET cAMP assays detect either Gs-coupled or Gi-coupled GPCRs; these GPCRs either stimulate or inhibit the formation of cAMP upon ligand binding. The researcher can monitor changes in cAMP levels by detecting competition between endogenously produced cAMP and biotinylated cAMP on anti-cAMP-conjugated "Acceptor" beads. The biotinylated cAMP forms a bridge between the Acceptor beads and "Donor" beads coated with streptavidin. As their name suggests, the Donor and Acceptor beads are respectively coated with fluorescent molecules (the donor and acceptor of a FRET couple) in which excitation of the donor at a wavelength of 680 nm results in emission of the acceptor at 520-620 nm when the beads are in close proximity. When non-biotinylated cAMP displaces the biotinylated variety, the beads are not bound together, FRET does not take place, and there is no acceptor fluorescence. Increased cAMP synthesis results in a lower fluorescent signal, while maximal signal is encountered in the absence of a Gs-coupled GPCR ligand or the presence of a strong Gi-coupled GPCR ligand.

By "high throughput screening" or "HTS" is meant that the assay is amenable to being performed using the same assay format and a large number of test compounds (or of samples prospectively containing such compounds) to quickly identify those compounds that are receptor ligands and differentiate them from those compounds that are not.

The number of compounds capable of being tested in a given time period may differ depending upon the characteristics of a given assay, the total number of compounds to be screened, and the sophistication of the assay equipment available. High throughput may be greater than about 100 compounds screened per day, greater than about 200 compounds screened per day, greater than about 500 compounds screened per day, greater than about 1000 compounds screened per day, greater than about 1500 compounds screened per day, greater than about 2000 compounds screened per day, or greater than about 10,000 compounds screened per day, greater than about 50,000 compounds screened per day. Partially or largely automated equipment is commercially available to permit the processing (assaying) of compounds with limited human intervention in the repetitive tasks of the assay necessary. A number of companies offer HTS services wherein the subscriber provides the receptor target or compound library, and the company will use their assay methodology and equipment to carry out the HTS.

Signals used to detect receptor activity are various. Two examples of such signals include those that result in pigment dispersion and those that cause alterations in calcium levels in the cell. Thus, the signal detected in some embodiments can be pigment dispersion and/or aggregation or ion- (for example, calcium-) mediated fluorescence. Such assays are well known to those of ordinary skill in the art. Where the signal is pigment dispersion and/or aggregation, the cells preferably are melaniferous and most preferably are lower animal pigment cells. Where the signal is calcium-mediated fluorescence, the cells can be virtually any cell known to those of ordinary skill in the art which exhibits, or can be made to exhibit, altered intracellular calcium levels (i.e., calcium flux) as a result of the activity of the receptor in question. Fibroblasts, 3T3 cells, lymphocytes, keratinocytes, etc., may be used. Mutated receptors also can be cloned into yeast cells, and assays involving the propagation of the yeast known to those of ordinary skill in the art can be employed as the detectable signal. Likewise, RSAT systems such as those described in U.S. Pat. No. 5,707,798, described and incorporated by reference above, can also be employed.

The present invention concerns, among other things, methods for determining whether a compound is a partial agonist of a cell surface receptor, comprising: contacting such compound with a cell surface receptor at room temperature (about 23° C.) and at least one higher temperature in the range about 23° C.—about 40° C. under conditions permitting a signal transduction activity of the receptor to be measured, wherein a lack of substantial activity at the lower temperature and the presence of measurable activity of such compound at the higher temperature indicates that such compound is a partial modulator agonist of such receptor.

Compounds may be screened against any GPCR according to the method of the invention, including alpha adrenergic receptors (e.g., alpha 1A, 1B, 1C, 2A, 2B, and 2C adrenergic receptors); beta adrenergic receptors (e.g., beta 1, 2, and 3 adrenergic receptors); cannabinoid receptors ("CB"), including CB1 and CB2; chemokine receptors, including chemokine C—X—C motif receptors ("CXCR") (e.g., CXCR1, CXCR2, CXCR3, and CXCR4), and chemokine C—C motif receptors ("CCR") (e.g., CCR1, CCR2, CCR3, CCR4, CCR5, CCR6, and CCR7); dopamine receptors, including dopamine D1, D2, D3, D4, and D5 receptors and their subtypes (e.g., the short and long variants of the dopamine D2 receptor, D2Sh and D2Lh, and the variants of the dopamine D4 receptor, D4.2, D4.3a, D4.3b, D4.4a, D4.4b, D4.4c, D4.4d, D4.4e, D4.5a, D4.5b, D4.6a, D4.6b, D4.7a, D4.7b, D4.7c, D4.7d, D4.8, and D4.10); endothelial differentiation sphingolipid receptors, including Edg1, Edg2, Edg3, Edg 4, Edg 5, Edg 6, Edg 7, and Edg 8 receptors; 5-hydroxytryptamine (serotonin) receptors, including $5HT_1$, $5HT_2$, $5HT_4$, $5HT_5$, $5HT_6$, and $5HT_7$ receptors and their subtypes (e.g., variants $5HT_{2A}$, $5HT_{2B}$, $5HT_{2C}$, $5HT_{5A}$ and $5HT_{5B}$, $5HT_6$, and $5HT_7$); γ-aminobutyric acid (GABA) G-protein coupled receptors, including the $GABA_B$ receptor; histamine receptors, including histamine $H_1$, $H_2$, $H_3$, and $H_4$ receptors; metabotropic glutamate receptors ("mGluRs"), including mGluR1, mGluR2, mGluR3, mGluR4, mGluR5, mGluR6, mGluR7, and mGluR8; opioid receptors, including opioid μ, κ, and δ receptors and their subtypes (e.g., μ1, μ2, κ1, κ2, κ3, δ1, and δ2) and the ORL 1 (orphanin) receptor; prostaglandin receptors, including prostaglandin CRTH2, DP, EP1, EP2, EP3, EP4, FP, IP, and TP receptors; somatostatin receptors, including SSTR1, SSTR2, SSTR3, SSTR4, and SSTR5I; tachykinin receptors, including neurokinin ("NK")$_1$, $NK_2$, and $NK_3$ receptors; and any of the GPCRs listed in Table 1, below. Compounds may be screened against any variant of these receptors, such as alternatively-spliced variants, chemical variants, and other variants.

Compounds used in methods of the invention may include members of a compound library, such as a combinatorial compound library. While diverse and broadly based compound libraries were at one time unusual and the result of years of effort, more recently myriad companies have been formed with a business plan largely involving offering compound libraries for biological screening purposes. For example, companies such as Specs (Delft, Netherlands) and TimTec, which is based in Russia, (U.S. address TimTec, Inc., 1300 First State Boulevard, Suite E, Wilmington, Del. 19804) offer libraries containing hundreds of thousands of compounds, targeted libraries (including libraries enriched for compounds having core structures known to interact with given receptor types). TimTec's targeted libraries include GPCR-targeted libraries, which contain compounds having core structures including the following:

TABLE 1

A compound library

| GPCR | Lattice type |
| --- | --- |
| CRF/NPY | Aryl-X-Aryl |
| CRF | 4-Aryl-2-aminothiazole |
| 5HT | Indolines |
| 5HT | gamma-Carbolines |
| 5HT | 5-Substituted indoles |
| 5HT | 4-ArylpiperazinesNH |
| 5HT | Aminoethylbenzamides |
| 5HT | Aminopropylbenzamides |
| BDZ-like | Fused 6,7 ring systems |
| Various | Spiro systems |
| Various | Aryl/Heteroarylpiperazines |
| Various | Benzylpiperazines |
| Various | 4-Aryl/heteroarylpiperidines |
| Various | 4-OH-4Phe-piperidines |
| Various | Tetrahydroisoquinolines |
| Chemokine | Diarylureas |

The companies named above, along with various other companies and academic institutions possess compound libraries, and have performed a structure-functional relationship analysis outlining the relationship between desired activity and given receptor types.

Thus, the choice of appropriate compounds to assay for partial agonist activity using the methods of the present invention, with a reasonable expectation of finding one or more such compounds, is now well within the skill of the person of ordinary skill in the art.

It is also important in the present methods that any cell line used for expressing the receptor of choice either inherently or recombinantly express any separate protein co-regulator A (such as a G-protein species that may be required for the desired activity of a given GPCR. Certain cell lines are known to inducibly or constitutively express certain G-proteins, such as Gq or Gi. However, if a given cell line does not normally express these proteins, the cell line may be transfected with an expression vector which will express the desired G-protein or other protein co-factor. Not all receptors (or all activities of receptors) will require the expression of a G-protein or other protein co-factor. In addition, one may transfect a cell with a G-protein (such as a chimeric G-protein) that is not normally found in that cell type in order to permit the receptor to couple to a new signaling pathway.

Consistent with the present invention is a method for the detection of modulators of a G-protein coupled receptor in a manner permitting the rapid screening of a large number of compounds comprising:
  a) contacting a cell expressing said receptor with a test compound, and
  b) detecting a change in the level of stimulation of such receptor in response to the presence of said test compound wherein both step a) and step b) are carried out at a temperature greater than 23° C. and less than 40° C.

By "rapid screening of a large number of compounds" is meant that the method can accommodate at least 100, or least 200, or at least 500, or at least 1000, or at least 1500, or at least 2000, or at least 10,000, or at least 50,000 compounds to be assayed in one day.

By "modulators" of a receptor activity is meant that the compound either increases or decreases the signaling response of the receptor as compared to the state of the receptor in the absence of a modulator. A simple competitive antagonist is not considered a modulator according to this definition, because it acts by merely blocking stimulatory or inhibitory signaling by such receptor.

By "endogenous" or "endogenously expressed" is meant that the cell expresses the indicated protein without being transfected with nucleic acid encoding such protein.

By "exogenous" or "exogenously expressed" is meant that a nucleic acid encoding the indicated protein is introduced into the cell thus permitting expression of such protein.

By "G-protein coupled receptor" or "GPCR" is meant a cell surface receptor member of the class of receptors known as "serpentine" receptors that contain helical domains which cross the plasma membrane seven times, and which coordinate with members of the class of GTP-binding proteins called G-proteins.

By "test compound" is meant any compound whose ability to stimulate or otherwise modulate a GPCR is sought to be determined and/or quantified.

By "detecting" a level of change in stimulation of a receptor is meant using any of a variety of means to determine whether the receptor is stimulated or de-stimulated. For example, and without limitation, stimulation of the receptor may result changes in conformation, phosphorylation, in levels of enzymatic activity, in formation of "second messengers" such as cAMP or in intracellular ion flux, (such as, without limitation, $Ca^{++}$, $Na^+$, $Cl^-$ or $K^-$).

Another method of the present invention includes a method for the detection of partial agonists of a G-protein coupled receptor comprising contacting a cell expressing said receptor with a test compound, and detecting a reproducible increase in the level of stimulation of such receptor in response to the presence of said test compound wherein, a) both said contacting and said detecting step are carried out at a first and second temperature,
 b) the first temperature is room temperature and the second temperature is a temperature greater than 23° C. and less than 40° C., and wherein if the activity of said compound is greater at the second temperature than at the first temperature, and said compound stimulates said receptor at a level less than about 40% of the native agonist of said receptor at said first temperature, said compound is identified as a partial agonist at said receptor.

In this method the ability of the agonist to stimulate the receptor is determined at room temperature and at a higher temperature. Those compounds that are found to reproducibly stimulate the receptor at the higher temperature are considered partial agonists of the receptor.

In an embodiment of the invention the method is adapted for the screening of at least 100, or at least 200, or at least 500, or at least 1000 or at least 2000, at least 10,000, or at least 50,000 compounds per day. As discussed above, in the last few years high throughput screening has become almost totally automated, with robotic equipment used to changes plates on the plate reader, to sample or read each well of the given plate, and with the resulting data being stored and analyzed on a computer. Thus, once the assays are established, and the plates are incubated, the conduct of the assay is capable of being performed by very few people, often only one or two people.

By "room temperature" is meant a temperature of about 23° C.

By "stimulation" of a receptor is meant to cause an increase in the intracellular cell-signaling cascade, regardless of whether such cascade ultimately results in the increase or decrease in synthesis, expression or release of an end product.

In certain embodiments of the present invention, an apparatus for carrying out high throughput FLIPR® assays at temperatures greater than room temperature (particularly, at about 37° C.) is provided.

Current HTS screening apparatuses such as the Analyst® system sold by Molecular Devices Inc., select and configure light sources, filters, detectors, and optical paths in an attempt to optimize assay performance. Such workstations are said to permit the generation of over 18,000 data points an hour. In addition to the analytical stage itself, which comprises a light source and various detectors, such a workstation may comprise a stacker that feeds 96-, 384- and/or 1536-well plates from a 20- or 40-plate magazine. The Analyst® apparatus processes over twelve 1536-well plates an hour. Additionally, various manufacturers, such as Beckman Coulter, Zymark, Thermo CRS and Tecan manufacture robotic HTS environments in which liquid addition and sample processing are handled using software and robotic machinery.

The Applicants contemplate that such systems can easily be made to exploit the present invention. For example, the stacker can be made to incorporate a heated stage (temperature adjustable), in which the plates are held at physiological temperature prior to reading. The analytical (optical) portion of the apparatus can also be manufactured to be held at the same temperature so as to insure against temperature variability between the stacker and the optical portion of the apparatus.

Alternatively, if space permits the apparatus (and any associated robotics) can be housed within a warm room of sufficient size to accommodate the samples and machinery.

In both of these latter two embodiments, preferably the temperature is greater than about 30° C. and below 40° C. Preferably, the temperature is between about 32° C. and about 37° C.; even more preferably between about 35° C. and about 37° C.; still more preferably, about 37° C. or precisely 37° C.

Other embodiments of the invention will be apparent from the disclosure.

Figure 3A:
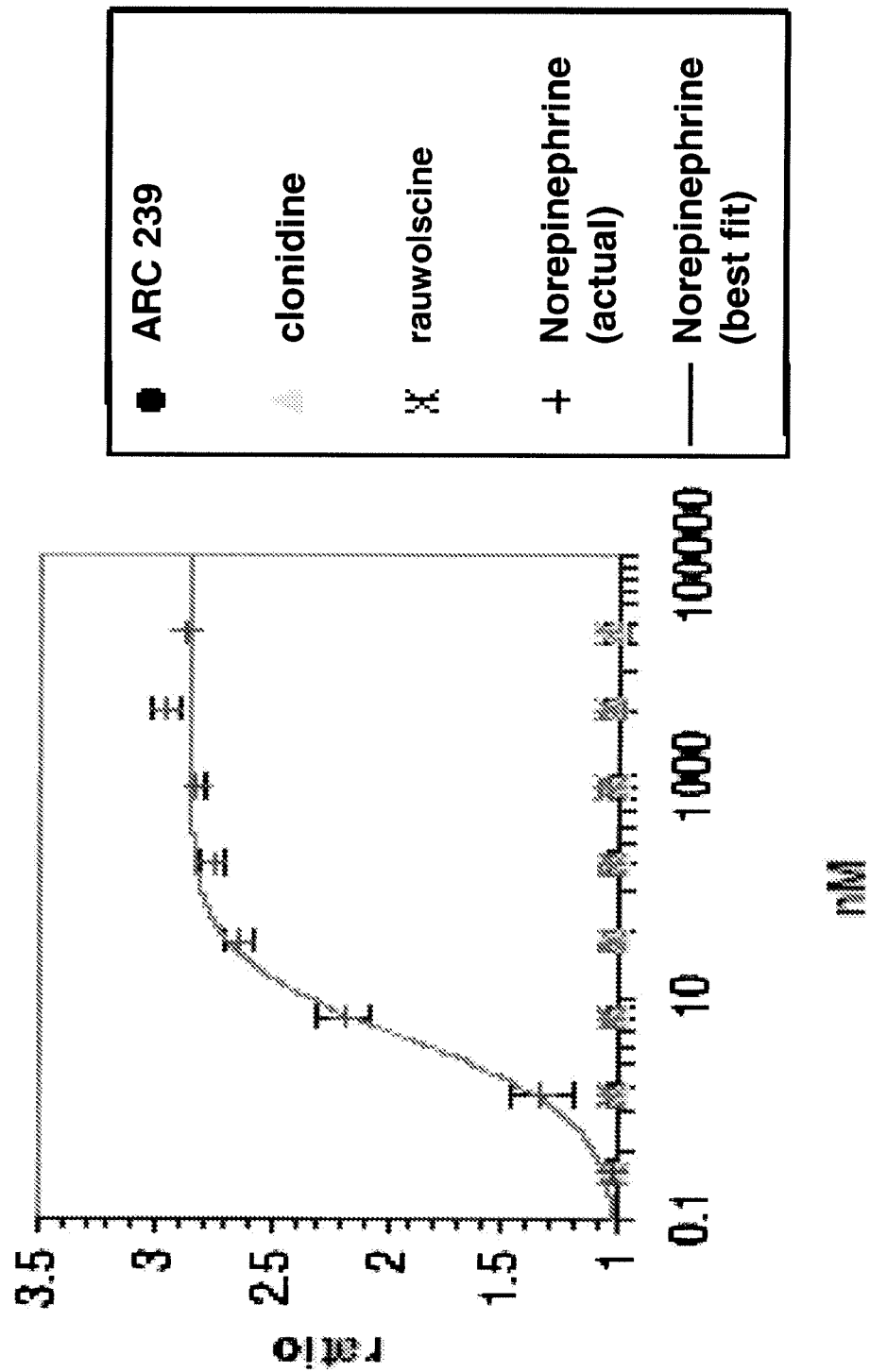
FIGS. 3A-3C show the results of a single experiment conducted at room temperature using the FLIPR methodology described in Example 1. The y-axis indicates the activity for that compound at the indicated concentration (ratio of peak height divided by the background fluorescence of the plate or microtiter well).

For FIG. 3A, compounds tested were ARC 239, which is an alpha 2B selective antagonist; clonidine (an alpha 2 pan agonist), rauwolscine (an alpha 2 antagonist), and norepinephrine.

Figure 3B:
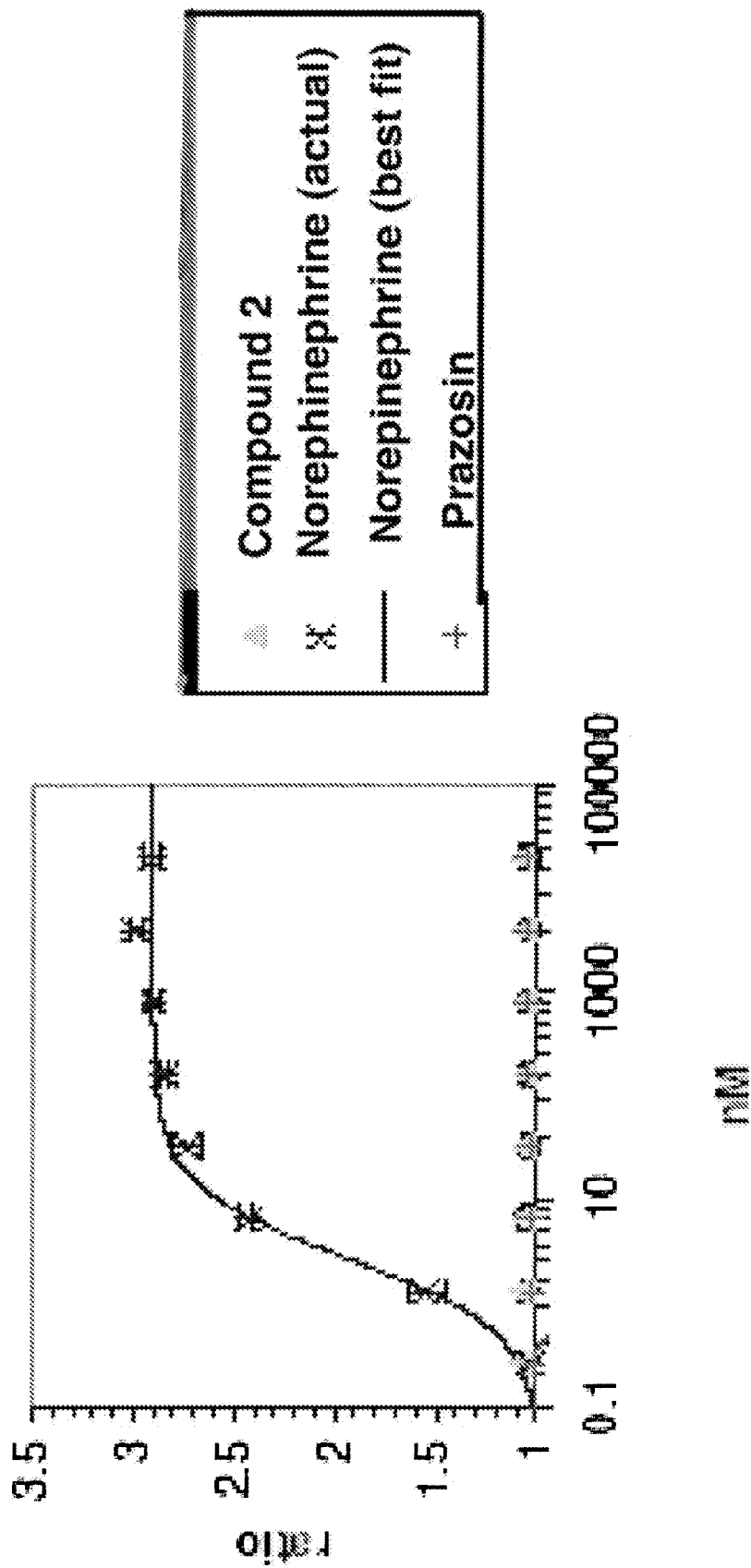

For FIG. 3B, the tested compounds were Compound 2, norepinephrine, and prazosin (an alpha 1 receptor antagonist).

Figure 3C:
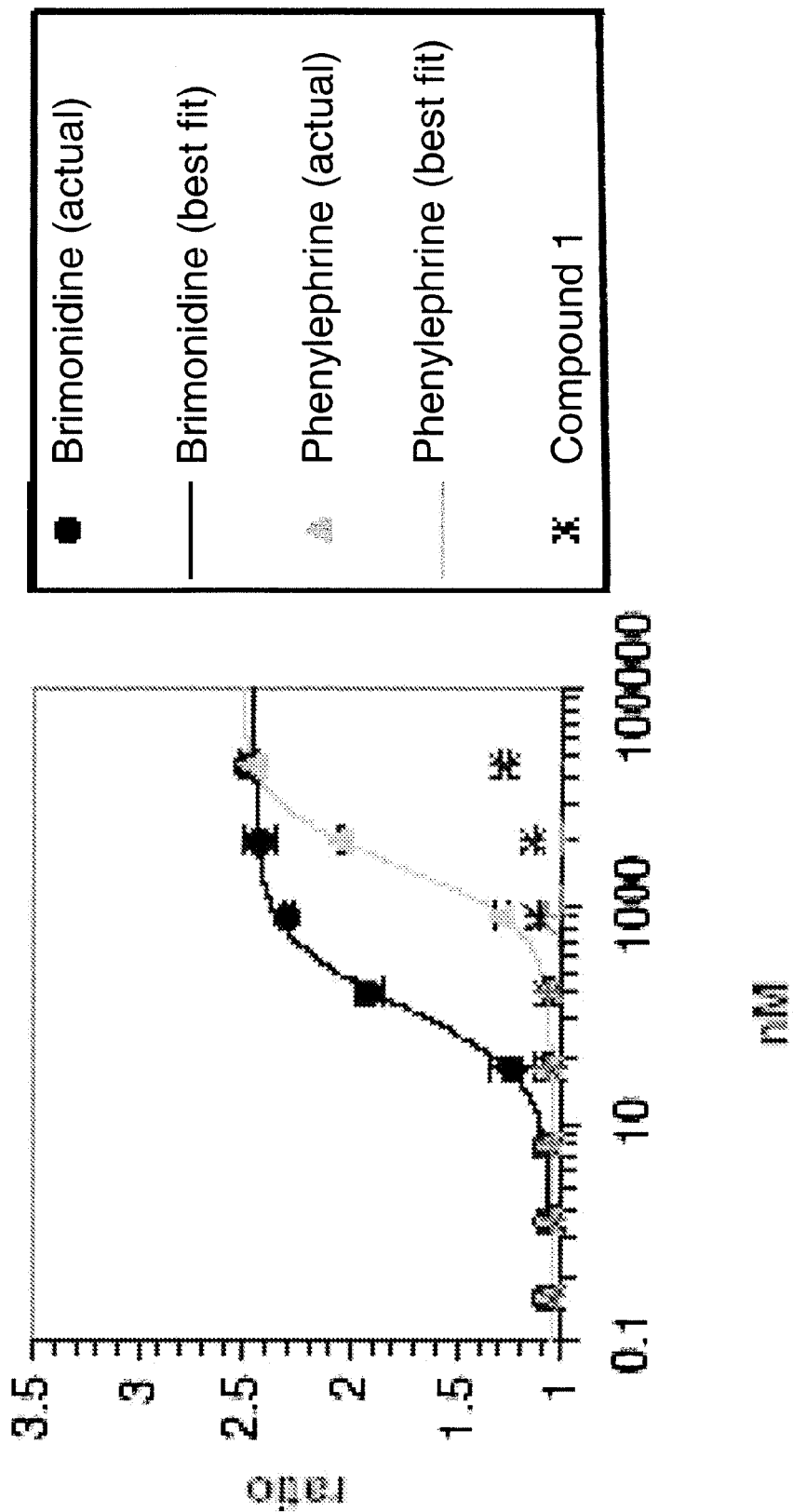

In FIG. 3C, the tested compounds were brimonidine, L-phenylephrine and Compound 1.

Figure 1:
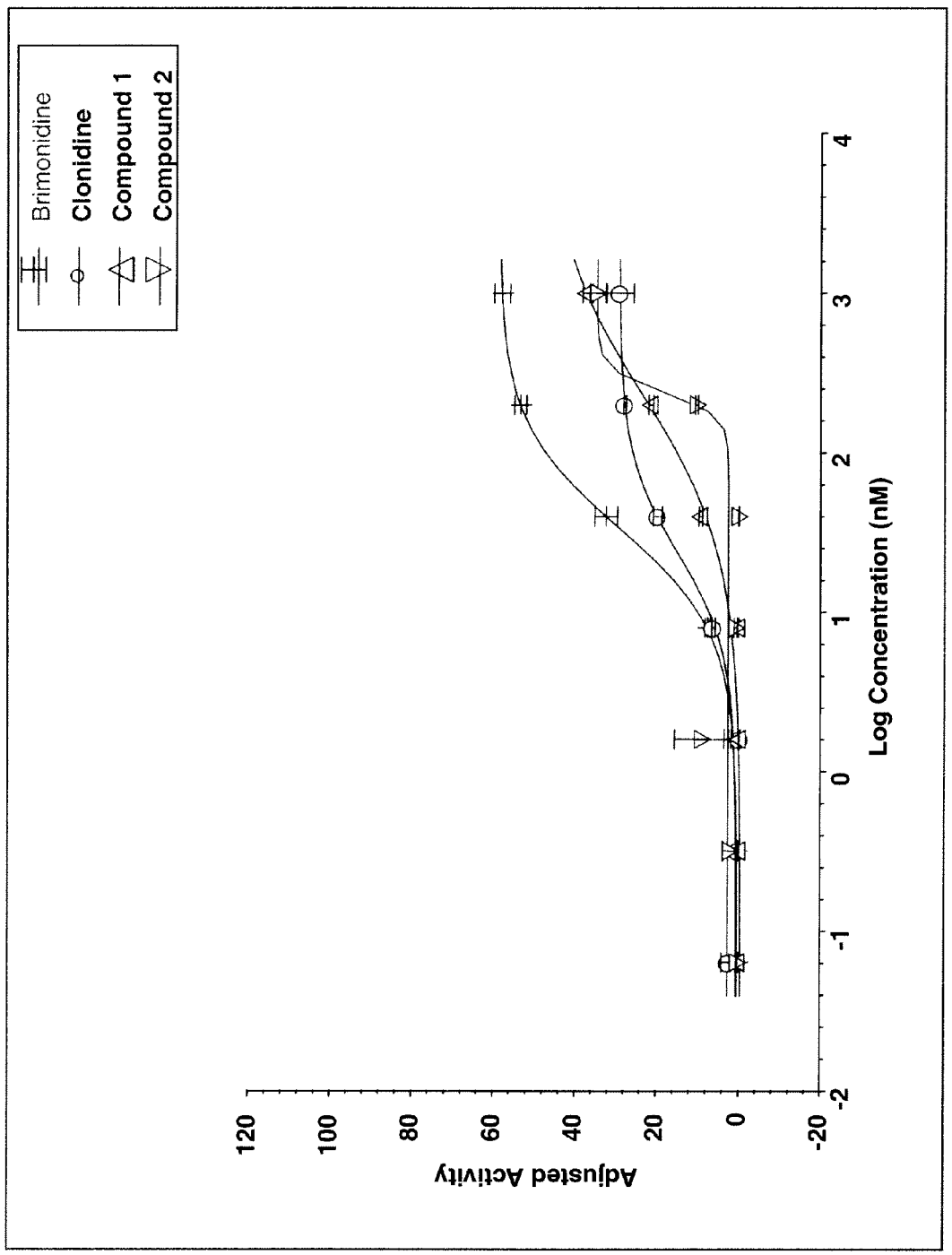
FIG. 1 shows a plot of activity versus concentration for brimonidine (an alpha 2 pan agonist), clonidine (an alpha 2 pan agonist), Compound 1 (a selective a2B agonist), and Compound 2 (a selective alpha 2B agonist). The assay was carried out at 35° C.
Figure 4C:
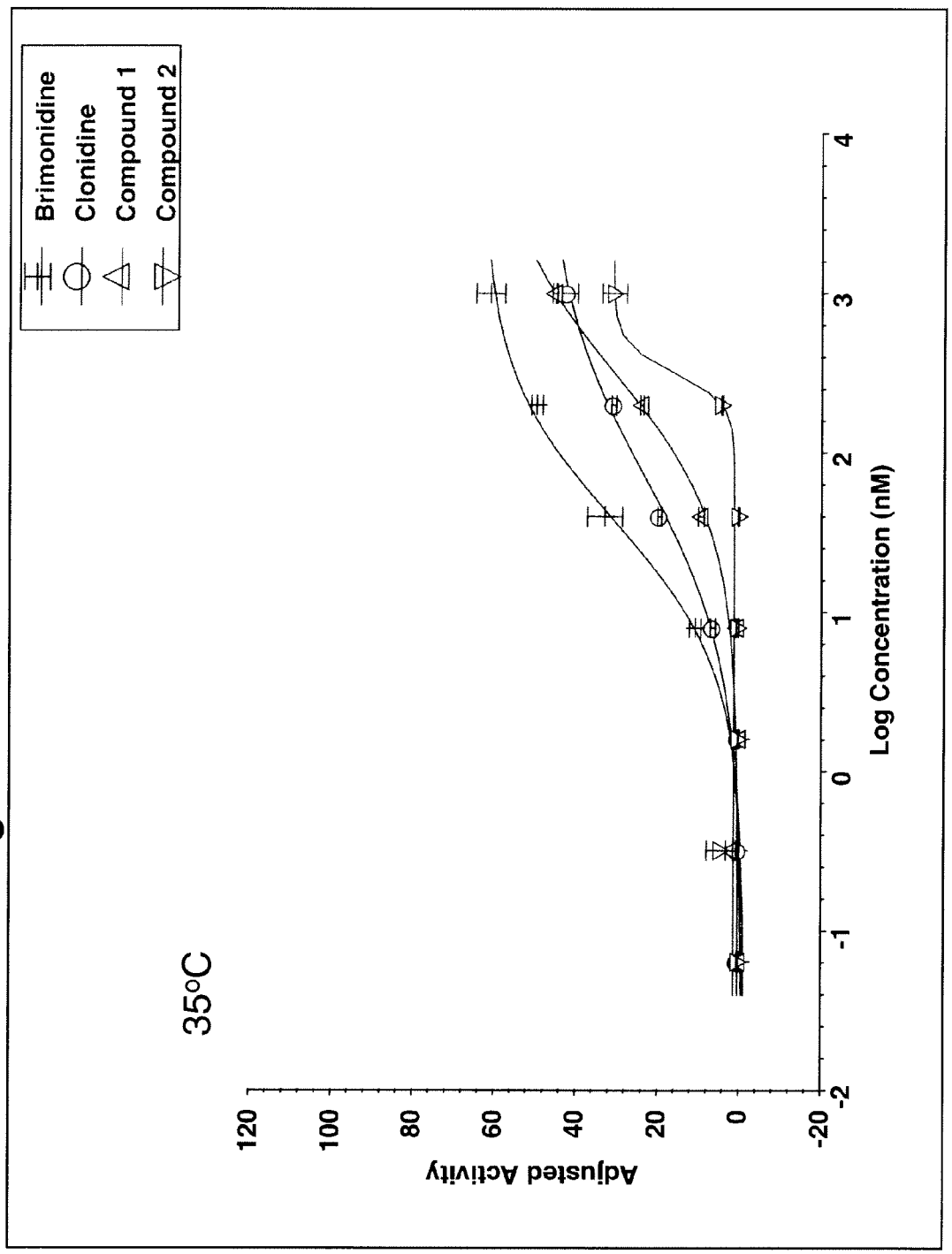
Figure 4D:
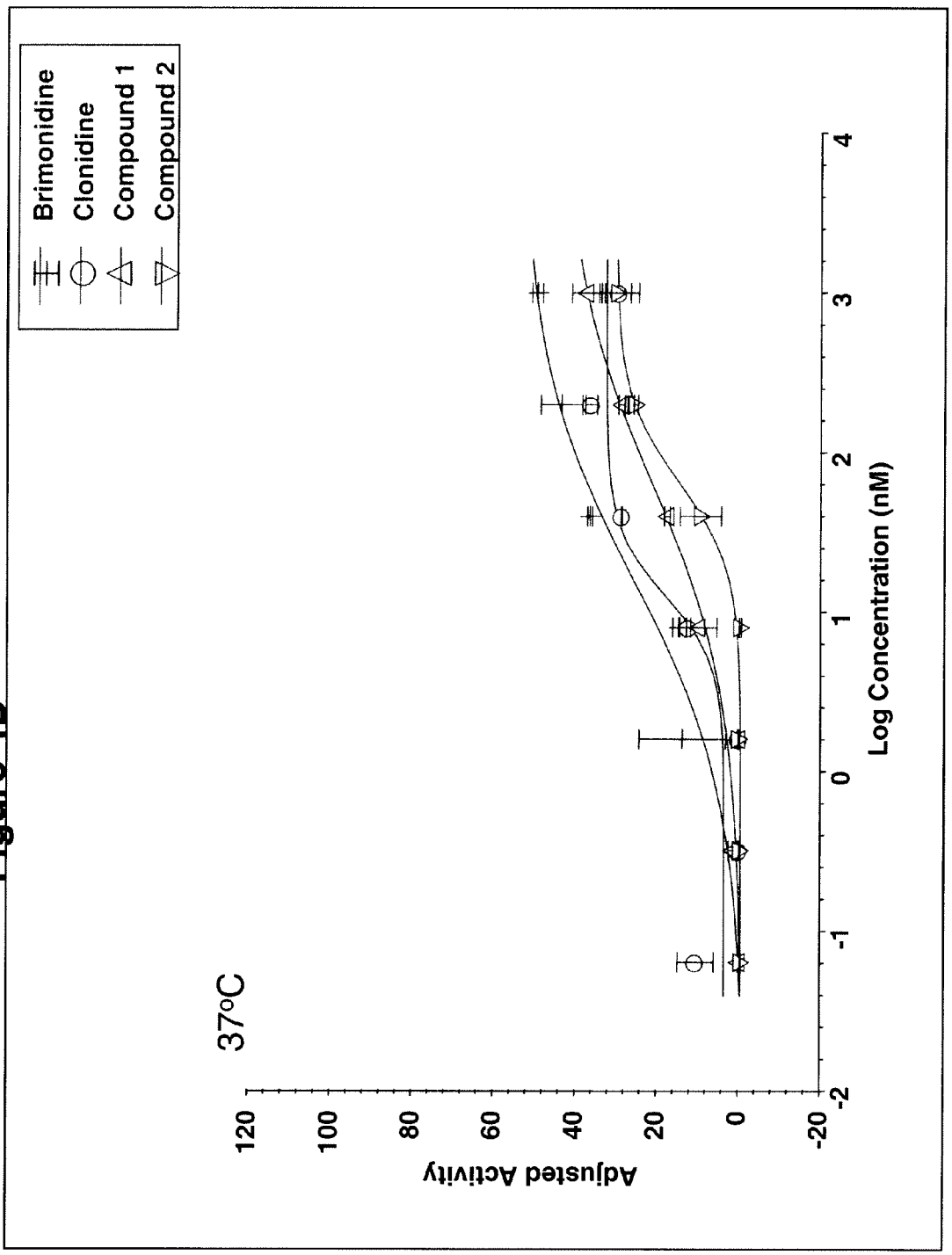

FIG. 4A-4D shows a plot of activity versus concentration for the same compounds in the same assay as that shown in FIG. 1. These experiments were performed, at room temperature (FIG. 4A), 32° C. (FIG. 4B), 35° C. (FIG. 4C), and 37° C. (FIG. 4D).

Figure 5:
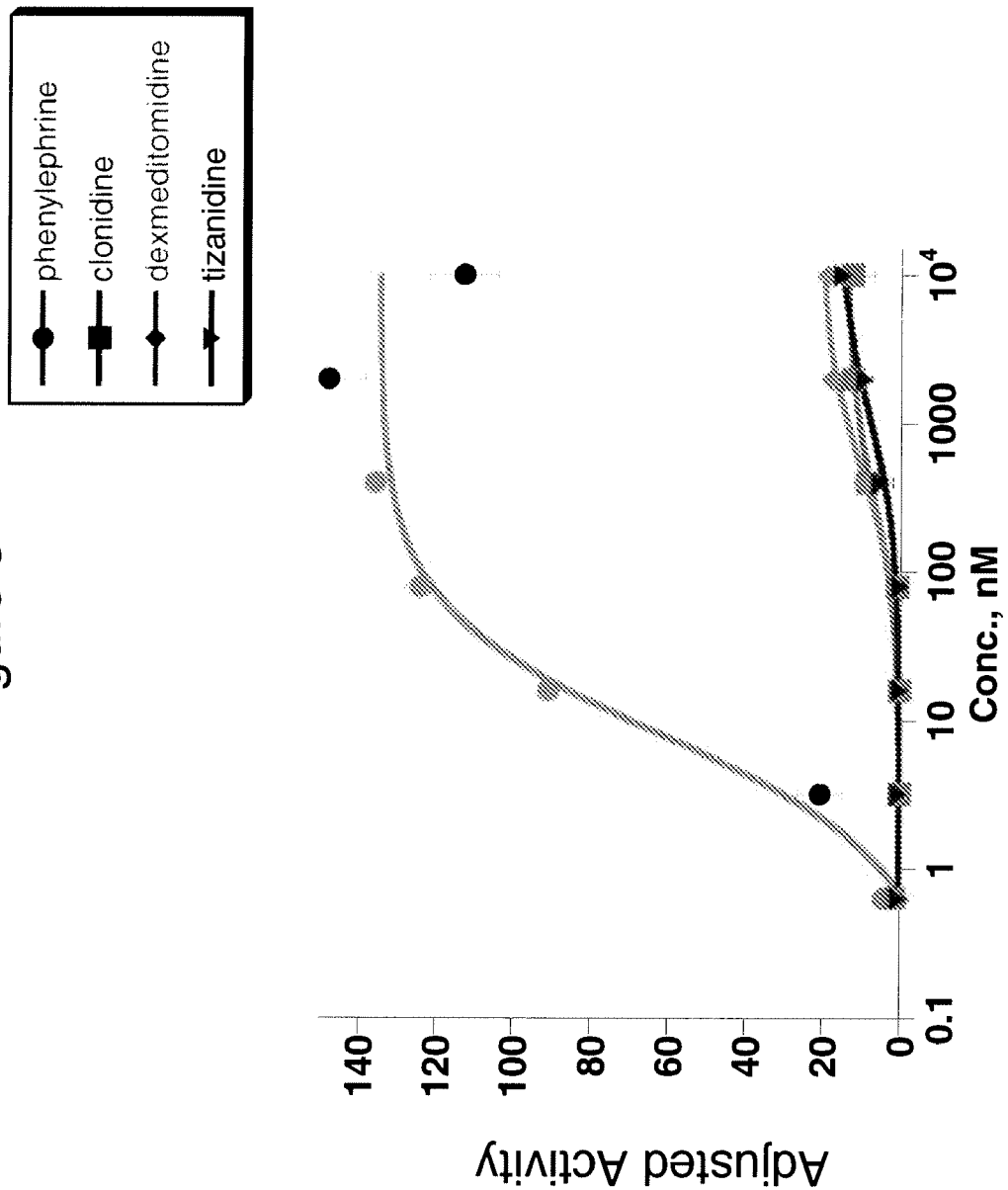

FIG. 5 shows a plot of activity versus concentration of brimonidine, clonidine, tizanidine, and dexmeditomidine at the alpha 1B receptor expressed in HEK 293 cells when the assay is conducted at room temperature.

Figure 6:
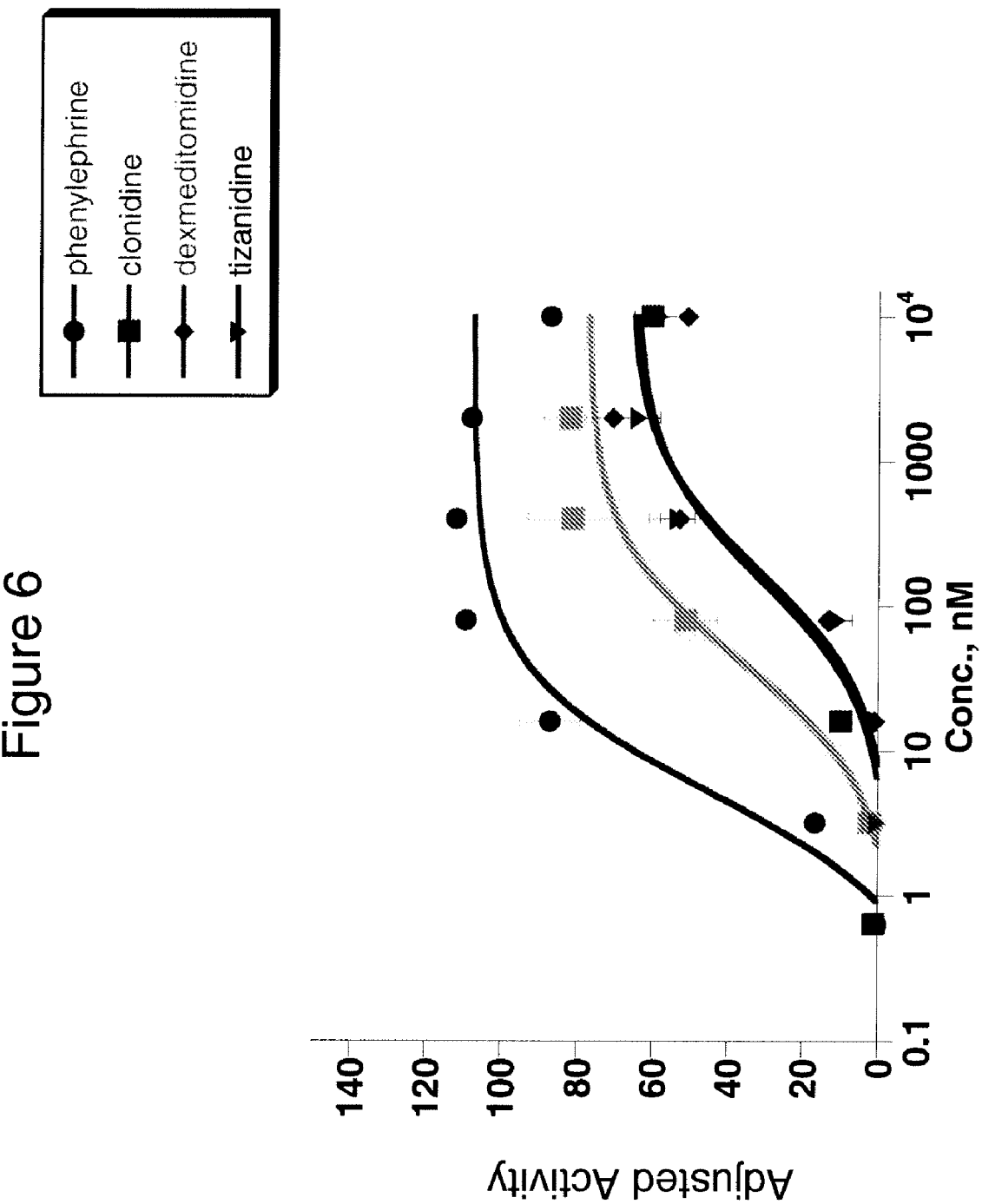

FIG. 6 shows a similar plot of the same experiment carried out at 35° C. The compounds used were the same as shown in FIG. 4.

EXAMPLES

Example 1

FLIPR Assay Methodology

This example describes the methodology used in assaying compounds for the ability to modulate the α2B receptor in a high throughput assay format in which the "readout" is the measurement of a change in intracellular calcium flux due to the use of the "promiscuous" Gqi5 hybrid G-protein, linking the α2B receptor (normally coupled to the adenylyl cyclase pathway) to the PLC pathway. Changes in intracellular calcium flux are monitored using a dye that becomes fluorescent when it binds free Ca$^{++}$ ion.

HEK 293 cells are stably co-transfected with two plasmids, the first encoding the mouse alpha 2B receptor (m α2B), and the second encoding the hybrid Gqi5 protein. The nucleotide sequence encoding the human α2B receptor is disclosed in Lomasney, J. W. et al., *Expansion Of The Alpha 2-Adrenergic Receptor Family: Cloning And Characterization Of A Human Alpha 2-Adrenergic Receptor Subtype, the Gene for which is located on Chromosome 2*, Proc. Natl. Acad. Sci. U.S.A. 87 (13), 5094-5098 (1990) and Regan, J. W. et al., *Cloning and expression of a human kidney cDNA for an alpha 2-adrenergic receptor subtype*, Proc. Natl. Acad. Sci. U.S.A. 85 (17), 6301-6305 (1988). The nucleotide sequence encoding the human Gqi5 protein is contained in the reference Aiyar et al., *Human AT1 receptor is a single copy gene: characterization in a stable cell line*. Mol. Cell. Biochem. 131: 75-86 (1994). These references are hereby all incorporated by reference herein. The resulting cells are termed "HEK 293 m α2B/Gqi5" cells. These cells are incubated in a 96 well plate using FLIPR buffer (Hank's Balanced Salt Solution plus 20 mM HEPES pH 7.4 and without sodium bicarbonate or phenol red).

The compounds tested are as follows:

a) Brimonidine

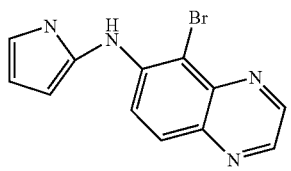

b) Clonidine

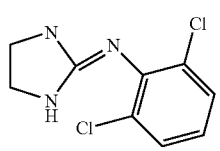

c) norepinephrine

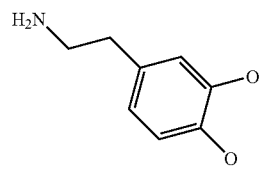

c) Rauwolscine

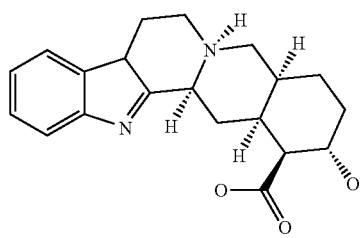

d) prazosin

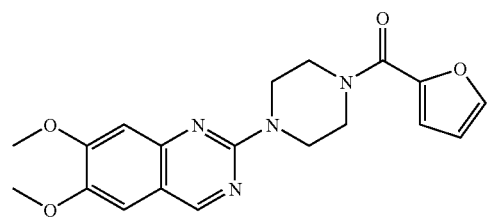

e) L-phenylephrine

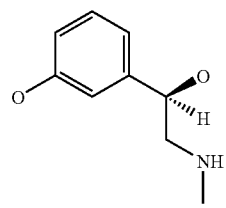

f) Compound 1

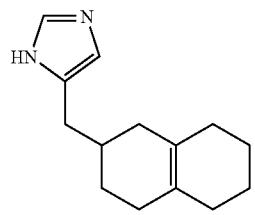

g) Compound 2

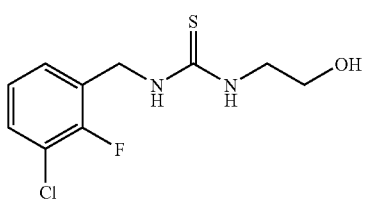

h) Compound 3

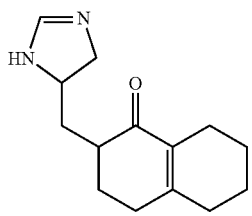

i) ARC 239

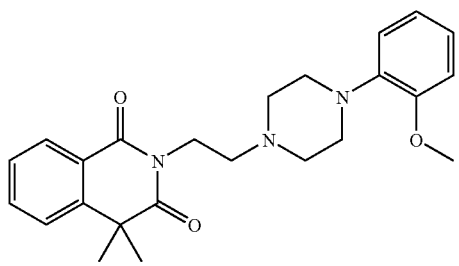

Each well of cells (in a 96 well microtiter dish) is assayed for activity in the FLIPR assay using the Fluo-4® calcium indicator dye to detect calcium flux. The structure of this dye, which can be purchased from Molecular Probes, Inc., is as follows:

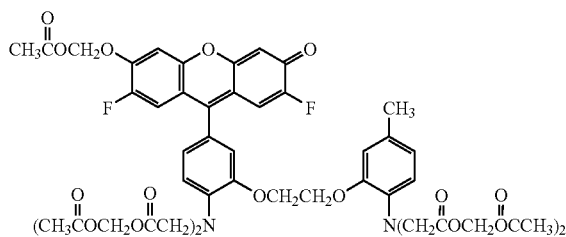

The cells are loaded with this dye using the manufacturer's recommendations, and washed 3× with FLIPR Buffer. Assays are conducted at room temperature (unless otherwise indicated in the following examples). Cells are then illuminated with an argon ion laser at 488 nm. Only cells releasing Ca++ into the cytosol of the cells (thereby permitting Ca++ binding to the Fluo-4 dye) will have increased fluorescent emission at 520 nm.

Images of the illuminated cells are captured with a charge-coupled device (CCD) camera; CCD technology is adapted for producing high-resolution images in conditions of ultra low light. Images are collected at the rate of 60 images/minute (1 image per second) in each well. After 10 seconds, 50 µl of the test compound is pipetted into the well, and further images are collected at 1 second intervals for an additional 60 seconds, then at 15 second intervals for 4 minutes. Test compounds are prepared from 10-2 M stocks in DMSO. Compounds are diluted in the FLIPR buffer to a final DMSO concentration of about 1%.

When 86 images have been collected, the positive control (a known receptor agonist) is added, and 130 more images are collected, first at 1-second intervals (70 images), then at 3 second intervals (60 images). All images are stored on a computer hard drive for later retrieval and analysis. From these images a plot of activity versus concentration is made for each compound, and the concentration of each compound at which 50% of that compound's maximal response is seen (the "$EC_{50}$") is calculated.

Example 2

Determination of $EC_{50}$ Values for "Tool Compounds"

FIG. 1 shows a plot of activity versus concentration for brimonidine (an alpha 2 pan agonist), clonidine (an alpha 2 pan agonist), Compound 1 (a selective alpha 2B agonist) and Compound 2 (a selective alpha 2B agonist), all tested at the α2B receptor. The $EC_{50}$ values for each compound were calculated for this assay system, and the relative efficacies compared to a norepinephrine standard are shown in parentheses; for brimonidine, the $EC_{50}$ is 43 nM (59%); for clonidine the $EC_{50}$ is 24 nM (29%); for Compound 1 the $EC_{50}$ is 238 nM (40%); and for Compound 2 it is 242 nM (35%). The assay was carried out at 35° C.

Figure 2:
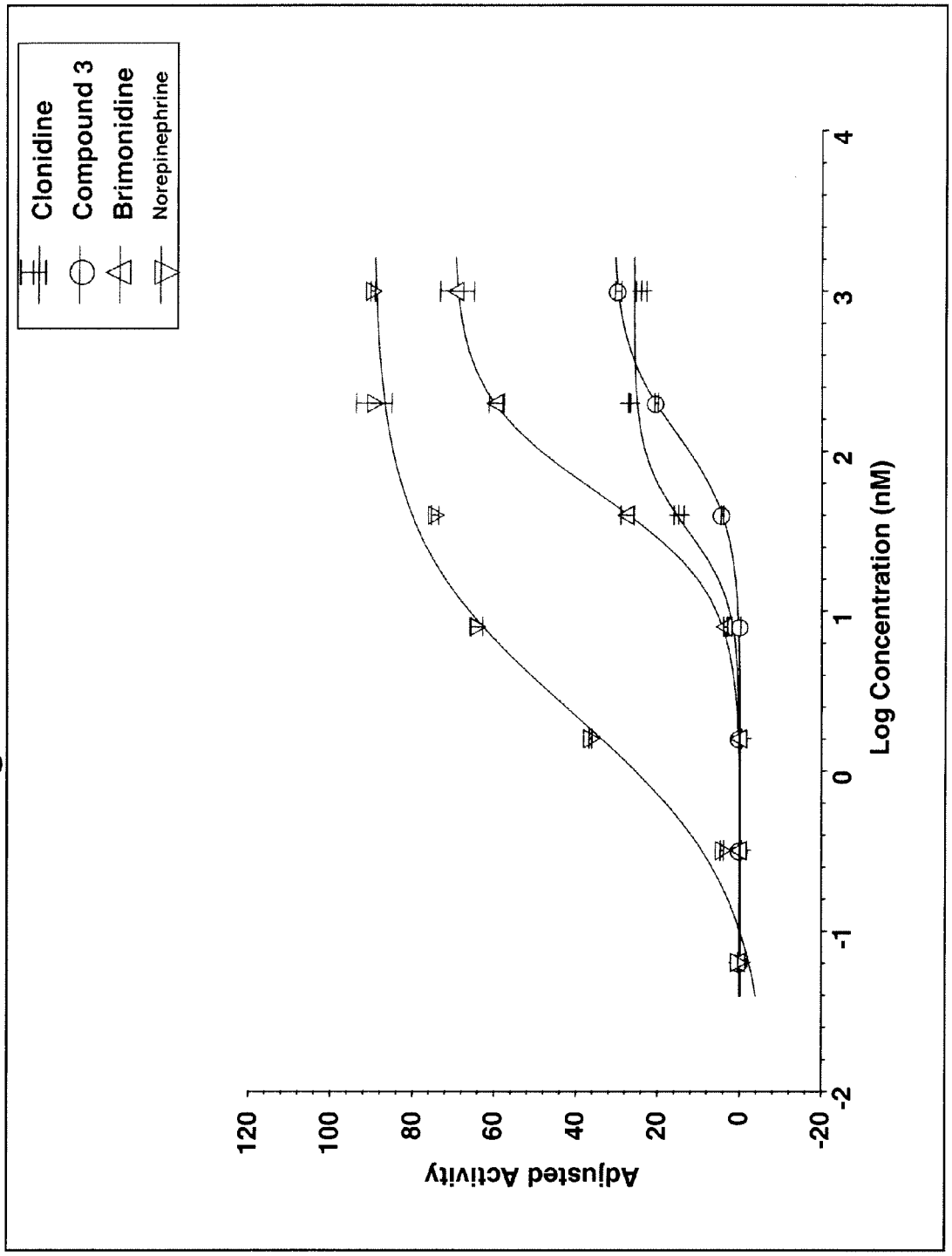
FIG. 2 shows a plot of activity versus concentration from a second experiment using norepinephrine, (an alpha1/alpha2 pan agonist) a positive control for agonist activity at the α2B adrenergic receptor, brimonidine, clonidine, Compound 3 (an alpha2B selective agonist).

FIG. 2 shows a plot from a second experiment, using norepinephrine as a positive control for agonist activity at the α2B adrenergic receptor. The experimental procedure was the same as for FIG. 1. In this experiment, the $EC_{50}$ and relative efficacy for brimonidine was 55 nM (70%); the $EC_{50}$ and relative efficacy for clonidine was 33 nM (26%); the $EC_{50}$ and relative efficacy for norepinephrine (an alpha1/alpha2 pan agonist) was 2 nM (90%); and the $EC_{50}$ and relative efficacy for Compound 3 (an alpha2B selective agonist) was 129 nM (31%).

FIGS. 3A-3B show the results of a single experiment conducted by a commercial "fee for services" screening company using the FLIPR methodology described in Example 1, except the assays were carried out at room temperature. These experiments were also carried out at the alpha 2B receptor. The plots are separated into three separate graphs to avoid confusion. The y-axis of the plots are labeled 1-3.5, and indicates the activity for that compound at the indicated concentration (ratio of peak height divided by the background fluorescence of the plate or microtiter well). For FIG. 3A, compounds tested were ARC 239, which is an alpha 2B selective antagonist; clonidine (an alpha 2 pan agonist), rauwolscine (an alpha 2 antagonist), and norepinephrine. At concentrations of from 1 to $10^4$ nM, only norepinephrine showed an activity ratio above background, while ARC 239 and rauwolscine showed no ability to stimulate alpha 2B receptor activity, as expected. Surprisingly, however, clonidine shows no activity in this assay, even though it is a known alpha 2 pan agonist.

For FIG. 3B, the tested compounds were Compound 2, norepinephrine, and prazosin (an alpha 1 receptor antagonist). In this plot, only norepinephrine shows activity above background. Compound 2, a known alpha B selective agonist, shows no activity in this assay.

In FIG. 3C, the compounds tested at the α2B receptor were brimonidine, L-phenylephrine, and Compound 1. In this plot, brimonidine showed activity at a maximum ratio of about 2.5 over background. Similarly, L-phenylephrine shows a maximum ratio of about the same. However, brimonidine has an $EC_{50}$ about 2-3 orders of magnitude less than L-phenylephrine, and is therefore more potent. Compound 2 shows very modest activity only at very high concentrations.

Comparison of the results shown in FIGS. 3A-3C with FIGS. 1 and 2 indicates that certain compounds, such as clonidine, Compound 1 and Compound 2, which show partial agonist activity in the experiments shown in FIGS. 1 and 2, do not show activity to any significant degree in the experiments shown in FIGS. 3A-3C. There were only a few differences between the assays—In the experiments shown in FIGS. 3A-3C the FLIPR buffer did not contain HEPES buffer; in these experiments a 384 well format (rather than a 96 well format used in the experiments correlating with FIGS. 1 and 2) was used. Finally, the experiments (i.e., the FLIPR analysis portion of these experiments) shown in FIGS. 1 and 2 were performed at 35° C. rather than at room temperature.

It appears that high throughput screening (particularly, though not exclusively in the FLIPR system) has traditionally been performed at room temperature. Heated plate heads (either 384 or 96 well) for the FLIPR apparatus have been considered incompatible with a stacker. Stackers are always, or almost always used in HTS; researchers often perform large runs using stackers and plates are often permitted to remain at room temperature for long periods of time (hours). Therefore, the manufacturer has in the past neither made assay equipment available that can read plates at temperatures other than room temperature, nor suggested that assays be performed at any temperature other than room temperature.

Recently a new FLIPR device has reportedly been made available; this equipment is said to be compatible with utilization of automation with a heated plate reader stage—mainly because certain dyes are said to be more active at elevated temperatures. However, the manufacturer has not suggested the detection of partial agonists or reverse agonists using the presently claimed assay methodology.

Example 3

Effect of Varying Temperature Upon Dose Response

In this experiment, the same compounds were used as shown in FIG. 1 and the experiments were carried out in the same manner, except in quadriplicate. One set of compounds were assayed at room temperature, another set were assayed at 32° C., the third set was assayed at 35° C., and the final set at 37° C. The results are shown graphically in FIGS. 4A-4D, respectively, and the data is provided in the Table below, with the figures representing the EC50 and relative efficacies in parenthesis.

| Compound | Room Temp. | 32° C. | 35° C. | 37° C. |
|---|---|---|---|---|
| Brimonidine | 78(63%) | 36(52%) | 38(63%) | 16(53%) |
| Clonidine | 120(5%) | 46(25%) | 74(40%) | 13(32%) |
| Compound 1 | 305(12%) | 302(30%) | 321(40%) | 67(40%) |
| Compound 2 | >1000 | 337(32%) | 318(31%) | 65(30%) |

These experiments clearly indicate that with rising temperature a gradual temperature-dependent increase in the activity of the partial agonists can be seen. There is an increased level of effect as well as activity at lower concentrations (leading to lower EC50 values) at higher temperatures at or close to physiological temperature.

Example 4

Detection of Alpha 1 Partial Agonists in a High Throughput FLIPR Screening Format The assay format was substantially similar to the assay format used for the detection of alpha 2B agonists described above, with the following exceptions. The cell line was again the HEK 293 cell line, this time stably transfected with the rat α 1B receptor gene, GenBank accession number BC070920, hereby incorporated by reference herein. The resulting cell line was termed HEK 293-α 1B. The α 1B receptor activates an intracellular calcium flux via endogenous Gq so there is no need to add an exogenous chimeric G-protein. Cells were cultured and challenged with various concentrations of the following compounds: phenylephrine, clonidine, dexmeditomidine, and tizanidine. The structures of the first two of these compounds are provided above. The structures of tizanidine and dexmeditomidine are as follows:

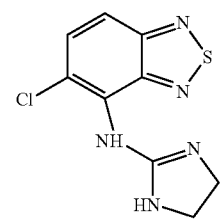

Tizanidine

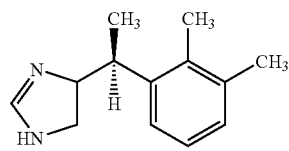

Dexmeditomidine

The assay was otherwise carried out using the Fluo-4 dye, argon laser excitation at 488 nm, and CCD camera detection essentially as described above, at room temperature, and at 35° C.

The results are shown in FIGS. 5 and 6. FIG. 5 shows the activity of these four compounds at the alpha 1 B receptor when the assay is conducted at room temperature. In this assay format, which corresponds to the assay format used for HTS of large numbers of compounds, only phenylephrine provides a clear indication of receptor activation, with a maximal signal of about 130% of that seen using a phenylephrine standard. In this and other experiments, the signal obtained from the standard may differ from that obtained from the same compound as an experimental, perhaps due to factors including location on the plate, illumination from the laser, cell to cell variation, pipetting error and the like.

Clonidine, dexmeditomidine and tizanidine all have similar maximal signals of about 15-20% of the phenylephrine when the assay is conducted at this temperature. EC50 values and relative efficacies (in parentheses) were as follows: phenylephrine: 8 nM (134%); clonidine: 320 nM (14%); dexmeditomidine: 486 nM (21%) and tizanidine: 1199 nM (17%).

By contrast, FIG. 6 shows the results of the same FLIPR assay of the same compounds, this time conducted at 35° C. rather than at room temperature. As can be seen, the plot and $EC_{50}$ for phenylephrine is essentially identical to those seen in FIG. 5. However, clonidine now appears to be quite an effective α 1B agonist, with an EC50 of 42 nM and a relative efficacy of 77% (as compared to phenylephrine). Dexmedi-tomidine and tizanidine show almost identical profiles at 37° C., have $EC_{50}$ values of 149 nM and 172 nM, respectively, and have relative efficacies in this assay system of 64% and 66%, respectively.

Thus, these data indicate that assays of alpha 1 receptor activity, like those of alpha 2 receptor activity, require assay temperatures greater than room temperature to detect partial agonists at these receptors. In each case, the assay at room temperature was able to detect full or particularly strong receptor agonists, but indicated that partial agonists of these receptors had little or no activity.

In addition, this experiment illustrates that the present invention is one of broad applicability. Indeed, with each receptor type in which the Applicants have tested the practice of comparing room temperature versus higher temperature in a HTS activity assay format, the higher temperature unmasked potential therapeutic compounds that that the room temperature assay failed to indicated as a potential agonist of particular value.

While the Examples have been provided to illustrate certain embodiments of the invention, its general applicability is not limited thereby, and the claims are to be construed as not being limited thereby.

We claim:

1. A high-throughput method for identifying partial agonists and partial antagonists of a G-protein coupled receptor, the method comprising the steps of
   a) contacting, at a temperature of about 25° C., a test compound with a cell expressing the receptor;
   b) detecting a change in the level of activity of the receptor;
   c) contacting, at a temperature of about 35° C., a test compound with a cell expressing the receptor;
   d) detecting a change in the level of activity of the receptor
   e) comparing the result obtained in step b) with the result obtained in step d) wherein a partial agonist or antagonist of the G-protein coupled receptor is identified if a compound shows no activity at a temperature of about 25° C. but does show activity at a temperature of about 37° C.

2. The method of claim 1 in which both of steps b) and d) comprises detecting a change in intracellular ion flux in said cell.

3. The method of claim 1 in which both of steps b) and d) comprises detecting a change in the level of intracellular second messengers in said cell.

4. The method of claim 1 wherein the G-protein coupled receptor is selected from the group consisting of an alpha adrenergic receptor, a beta adrenergic receptor, a cannabinoid receptor, a chemokine receptor, a dopamine receptor, an endothelial differentiation sphingolipid receptor, a 5-hydroxytryptamine G-protein coupled receptor, a y-aminobutyric acid G-protein coupled receptor, a histamine receptor, a metabotropic glutamate receptor, an opioid receptor, a prostaglandin receptor, a somatostatin receptor, and a tachykinin receptor.

* * * * *

UNITED STATES PATENT AND TRADEMARK OFFICE
CERTIFICATE OF CORRECTION

PATENT NO. : 7,655,396 B1  
APPLICATION NO. : 11/855858  
DATED : February 2, 2010  
INVENTOR(S) : Karen M. Kedzie et al.

Page 1 of 3

It is certified that error appears in the above-identified patent and that said Letters Patent is hereby corrected as shown below:

On the Title page, under "Other Publications", in column 2, line 4, delete "Biochem" and insert -- Biochem. --, therefor.

On the Title page, under "Other Publications", in column 2, line 6, delete "characteriazation" and insert -- characterization --, therefor.

Drawings  
In Sheet 4 of 11, Figure 3B, line 5, delete "Norephinephrine" and insert -- Norepinephrine --, therefor.

In Sheet 10 of 11, Figure 5, line 3, delete "dexmeditomidine" and insert -- dexmedetomidine --, therefor.

In Sheet 11 of 11, Figure 6, line 3, delete "dexmeditomidine" and insert -- dexmedetomidine --, therefor.

In column 2, line 43-44, delete "bronchodialator" and insert -- bronchodilator --, therefor.

In column 4, line 24, delete "chloronaphthole," and insert -- chloronaphthol, --, therefor.

In column 5, line 34, delete "EAAT 1, EAAT 2" and insert -- EAAT1, EAAT2 --, therefor.

In column 5, line 39, delete "Na+/K+" and insert -- $Na^+/K^+$ --, therefor.

In column 5, line 46, delete "amylotropic" and insert -- amyotrophic --, therefor.

In column 5, line 60, delete "(Delbecco's" and insert -- (Dulbecco's --, therefor.

In column 6, line 19, delete "10" and insert -- 100 --, therefor.

In column 6, line 51, delete "an" and insert -- a --, therefor.

Signed and Sealed this

Fifteenth Day of June, 2010

David J. Kappos  
*Director of the United States Patent and Trademark Office*

In column 7, line 28, delete "7.5" and insert -- 7.5. --, therefor.

In column 7, line 29, delete "($^3$H]" and insert -- [$^3$H] --, therefor.

In column 7, line 47, delete "Disrupter" and insert -- Disruptor --, therefor.

In column 7, line 57, delete "propanolol," and insert -- propranolol, --, therefor.

In column 9, line 33-34, delete "Edg 4, Edg 5, Edg 6, Edg 7," and insert -- Edg4, Edg5, Edg6, Edg7, --, therefor.

In column 9, line 34, delete "Edg 8" and insert -- Edg8 --, therefor.

In column 12, line 45, delete "a2B" and insert -- α2B --, therefor.

In column 13, line 7, delete "dexmeditomidine" and insert -- dexmedetomidine --, therefor.

In column 15, line 4-11, delete " [structure] " and insert -- [structure] --, therefor.

In column 15, line 49, delete "Ca++" and insert -- Ca$^{++}$ --, therefor.

In column 15, line 50, delete "Ca++" and insert -- Ca$^{++}$ --, therefor.

In column 17, line 37, delete "quadriplicate." and insert -- quadruplicate. --, therefor.

In column 17, line 42, delete "EC50" and insert -- EC$_{50}$ --, therefor.

In column 17, line 58, delete "EC50" and insert -- EC$_{50}$ --, therefor.

In column 18, line 3, delete "α 1B" and insert -- α1B --, therefor.

In column 18, line 5, delete "α 1B." and insert -- α1B. --, therefor.

In column 18, line 5, delete "α 1B" and insert -- α1B --, therefor.

In column 18, line 9-10, delete "dexmeditomidine," and insert -- dexmedetomidine, --, therefor.

In column 18, line 12, delete "dexmeditomidine" and insert -- dexmedetomidine --, therefor.

In column 18, line 29-34, delete " 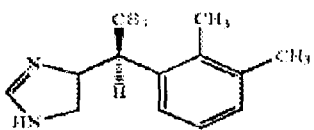 " and insert

-- 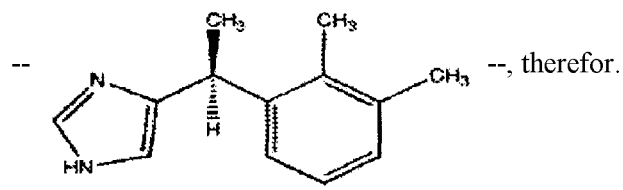 --, therefor.

In column 18, line 37, delete "Dexmeditomidine" and insert -- Dexmedetomidine --, therefor.

In column 18, line 44, delete "1 B" and insert -- 1B --, therefor.

In column 18, line 55, delete "dexmeditomidine" and insert -- dexmedetomidine --, therefor.

In column 18, line 57, delete "EC50" and insert -- $EC_{50}$ --, therefor.

In column 18, line 59-60, delete "dexmeditomidine:" and insert -- dexmedetomidine: --, therefor.

In column 18, line 67, delete "α 1B" and insert -- α1B --, therefor.

In column 18, line 67, delete "EC50" and insert -- $EC_{50}$ --, therefor.

In column 19, line 1-2, delete "Dexmeditomidine" and insert -- Dexmedetomidine --, therefor.

In column 20, line 24, in Claim 4, delete "y-aminobutyric" and insert -- γ-aminobutyric --, therefor.